US00PP10958P

United States Patent [19]

Wain

[11] Patent Number: Plant 10,958

[45] Date of Patent: Jun. 15, 1999

[54] CHRYSANTHEMUM PLANT NAMED 'BLUSH HAWAII'

[75] Inventor: Peter Wain, Portsmouth, United Kingdom

[73] Assignee: Cleangro, Ltd., West Sussex, United Kingdom

[21] Appl. No.: 08/968,605

[22] Filed: Nov. 13, 1997

[51] Int. Cl.[6] ..... A01H 5/00

[52] U.S. Cl. ..... Plt./291

[58] Field of Search ..... Plt./80, 81, 291, Plt./292, 287

[56] References Cited

PUBLICATIONS

UPOU-ROM, 1998/01, Plant Variety Database, GTT Jouve Retrieval Software, 2 citations for 'Blush Hawaii'.

*Primary Examiner*—Howard J. Locker

*Attorney, Agent, or Firm*—Christie, Parker & Hale, LLP

[57] ABSTRACT

A new plant variety of Chrysanthemum producing pink flowers.

1 Drawing Sheet

BACKGROUND OF THE INVENTION

The present invention is directed to a new and distinct variety of Chrysanthemum botanically classified as *Dendranthema grandiflora*. The varietal denomination of the new Chrysanthemum is 'Blush Hawaii'.

The new variety was discovered as a single branch in a controlled planting of the unpatented variety 'Hawaii'. The new variety has been asexually reproduced by vegetative cuttings in Ventura County, Calif. and the distinguishing characteristics are retained through successive generations of asexual reproduction.

SUMMARY OF THE INVENTION

'Blush Hawaii' is a spray type cut flower Chrysanthemum plant variety that produces pink flowers and dark green foliage.

COMPARISON

The new variety differs from its parent in having strong blush pink tones in the petals and a larger darker center. The flower is also larger and the plant is more vigorous, with a greater number of breaks from pinching and more flowers per branch.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of December. 'Blush Hawaii' has not been observed under all possible environmental conditions. The phenotype may vary with variations in the environment such as temperature, light intensity, day length and cultural conditions. In the following description color is described by reference to The Royal Horticultural Society Colour Chart.

To produce a commercial product the plants may be pinched once and center bud removed. It has been observed that the shelf life of 'Blush Hawaii' is about 29 days with the response time of about 9 weeks. One application of growth retardant B-9 at 2000 ppm may be used.

PLANT

Habit: Upright.

Height: About 86 cm after on application of growth regulator as described.

Number of breack from pinch: About 3 per.

Stem color: Near 146C.

FOLIAGE

Leaf Arrangement: Alternate.

Number of leaves per lateral branch:

*Average number leaves per lateral branch.*—About 24, many leafy side branches.

(1) *Size.*—Length — Average about 15.3 cm. Width — Average about 8.6 cm.

(2) *Shape.*—Ovate.

(3) *Attachment.*—Petioled.

(4) *Apex.*—Acute with serration at tip.

(5) *Base.*—Tapered.

| (6) Color: | Mature | Young |
|---|---|---|
| Top: | Near 137A | Near 137A |
| Bottom: | Near 138B | Near 138C |

Margin: Deeply lobed with slight serrations.

Aspect: Cupped at base of leaf.

Surface characteristics: Top-puberulent with waxy appearance, bottom-puberulent.

Venation: Palmately net, main veins prominent on underside of leaf, main vein coloration near 143D, veinlet coloration near 137D.

Petiole:

(1) *Length.*—About 3 cm average.

(2) *Color.*—Near 146D.

(3) *Other characteristics.*—Very sturdy and reflexed back.

Stipule: 2 per mature leaf; large, leafy, 4-lobed with 2 lobes being deeper.

FLOWER

Inflorescence form: Cyme.

Flower form: Decorative.

Flower color (general): Pink decorative with darker center.

Blooms: About 18 blooms average per branch.

(1) *Diameter.*—Average about 9 cm.

(2) *Depth.*—Average about 3 cm.

Sepal:

(1) *Number.*—About 40.

(2) *Color.*—Near 137C.

(3) *General appearance.*—Thin and membranous.

Peduncle:

(1) *Length.*—About 8 cm at top, about 17 cm further down stem.

(2) *Habit.*—Very slight irregular curve.

(3) *Surface.*—Highly puberulent.

(4) *Color.*—Near 137D.

(5) *Strength.*—Strong especially at top, lower peduncles sturdy considering length.

Ray florets:

(1) *Number per flower.*—Average about 230.

(2) *Texture.*—Slight shine.

(3) *Shape.*—Broadly elliptic.

(4) *Apex.*—Small acute tip, no prominent lobes.

(5) *Base.*—Tapered.

(6) *Margin.*—Entire.

(7) *Aspect.*—Strongly curved under.

(8) *Length.*—Avg. About 4.2 cm.

(9) *Width.*—Avg. About 1.3 cm average.

*Color*— top side.—Immature: Near 29 D with near 37C tip. Mature: Near 56D with near 56A tip. Fading: To near 56D.

*Color* — under side.—Immature: Near 158D with 70B streak down center. Mature: Near 76D with 72D streak down center. Fading: Near 56D.

Disc florets: Not present.

REPRODUCTIVE ORGANS

Ray florets:

*Pistillate.*—(1) Pistil number: 1 per flower. (2) Ovary shape: One half sphere with pointed apex. (3) Stigma shape: Curled. (4) Stigma color: Near 9A. (5) Style length: Average about 0.6 cm. (6) Style color: Near 154C.

What is claimed is:

1. A new and distinct variety of Chrysanthemum plant substantially as herein shown and described.

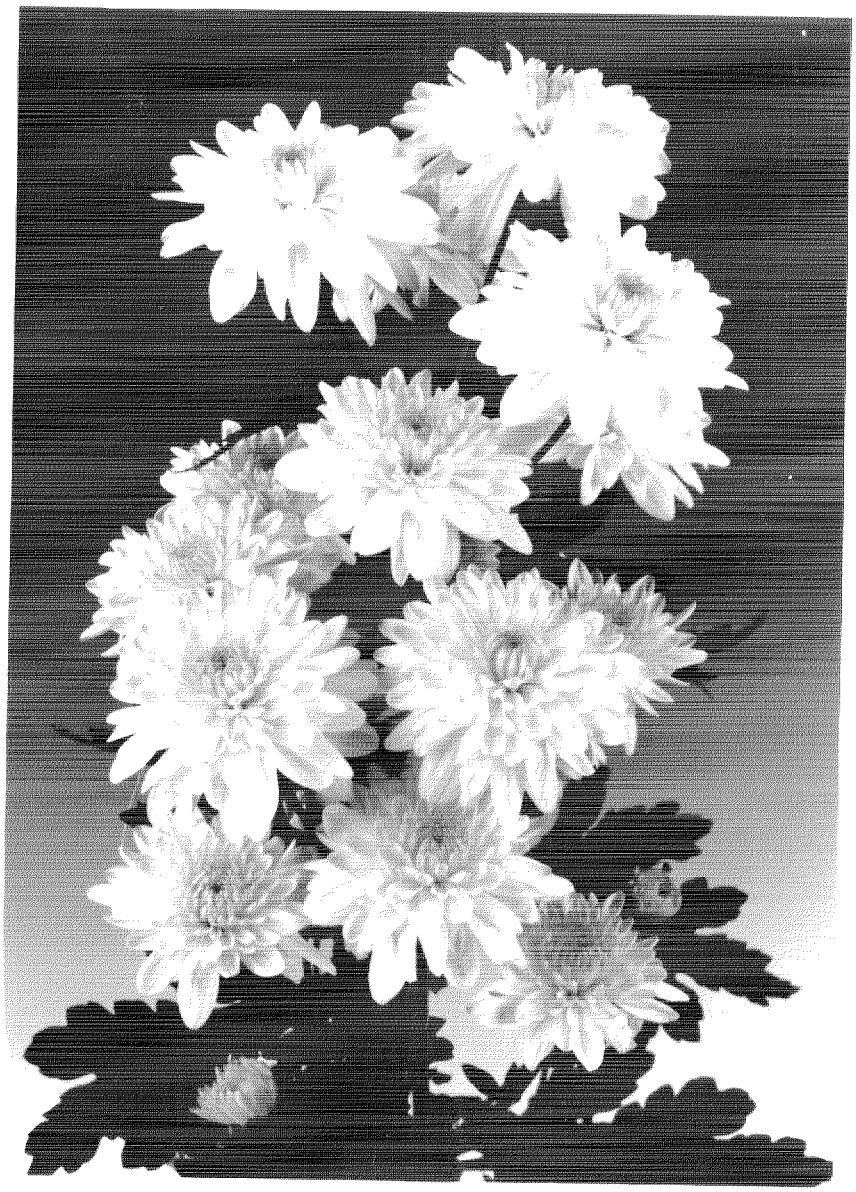

* * * * *